United States Patent [19]

Sorvillo et al.

[11] Patent Number: 5,190,858
[45] Date of Patent: Mar. 2, 1993

[54] MONOCLONAL ANTIBODIES DIRECTED TO EPITOPES OF HUMAN TRANSFORMING GROWTH FACTOR—α AND USES THEREOF

[75] Inventors: John M. Sorvillo, Merrick; David M. Valenzuela, Franklin Square; Frederick H. Reynolds, Jr., Syosset, all of N.Y.

[73] Assignee: Oncogene Science, Inc., Uniondale, N.Y.

[21] Appl. No.: 304,947

[22] Filed: Feb. 1, 1989

[51] Int. Cl.$^5$ .................. C12Q 1/00; G01N 33/53
[52] U.S. Cl. .................. 435/7.23; 435/7.1; 435/7.21; 435/172.1; 435/172.2; 435/70.21; 436/518; 436/535; 530/388.8
[58] Field of Search .................. 435/7, 172.1, 172.2; 436/536, 518, 535; 530/387

[56] References Cited

PUBLICATIONS

Kobrin et al. —Chem. Abst. vol. 105 (1986), p. 219,710h.
Banks et al. —Chem. Abst. vol. 105(1985), p. 155,264h.
Toyo—Chem. Abst. vol. 102 (1985), p. 92518a.
Toyo—Chem. Abst. vol. 103(1985), p. 1271w.
Derynck, R., et al., Cell, 38:287 (1984) (Exhibit B).
Bringman, T. S., et al., Cell, 48:429 (1987) (Exhibit C).
Gottlieb, A., et al., J. Exp. Med., 167:670 (1988) (Exhibit D).
Coffey, R. J. Jr., et al., Nature, 328:817 (1987) (Exhibit E).
Kobrin, M. S., et al., Endocrinology, 121:1412 (1987) (Exhibit F).
Kudlow, J. E., et al., Endocrinology, 121:1577 (1987) (Exhibit G).
Kobrin, M. S., et al., J. Biol. Chem., 261:14414 (1986) (Exhibit H).

Primary Examiner—Sam Rosen
Attorney, Agent, or Firm—John P. White

[57] ABSTRACT

The present invention provides a monoclonal antibody which specifically forms a complex with TGFα in formalin-fixed, paraffin-embedded tissue sections which has an affinity of a least $10^7$, and which is directed to the epitope to which monoclonal antibody 213-4.4 (ATCC No. HB9992) is directed. The invention further provides the above-described monoclonal antibody wherein the epitope consists essentially of amino acids 34–43 of TGFα.

Additionally, the invention concerns the monoclonal antibody 213-4.4 (ATCC No. HB9992).

The invention also provides a method of detecting TGFα in tissue sections of a tissue in which normal tissue is characterized by the absence of TGFα and neoplastic tissue is characterized by the presence of TGFα in a subset of such neoplastic tissue which comprises contacting the tissue sections with an antibody directed to an epitope on TGFα under conditions such that the antibody binds to the tissue sections detecting the antibody bound to the tissue sections and thereby detecting TGFα in the tissue sections.

The invention further provides the monoclonal antibody 134A-2B3 (ATCC No. HB9993). Additionally, the invention concerns the monoclonal antibody 137-178 (ATCC No. HB9994).

14 Claims, 2 Drawing Sheets

5,190,858

MONOCLONAL ANTIBODIES DIRECTED TO EPITOPES OF HUMAN TRANSFORMING GROWTH FACTOR—α AND USES THEREOF

BACKGROUND OF THE INVENTION

Throughout this application, various publications are referenced by Arabic numerals with parentheses. Full citations for these publications may be found at the end of the specification immediately preceding the claims. The disclosures of these publications in their entireties are hereby incorporated by reference into this application in order to more fully describe the state of the art as known to those skilled therein.

The term transforming growth factor (TGF) has been applied to peptides that have the ability to confer the transformed phenotype on untransformed fibroblastic indicator cells in vitro. In the early 1980's it was suggested that polypeptide growth factors secreted by a cell might play a part in malignant transformation of that cell. The demonstration that many virally transformed cells which had reduced levels of assayable receptors for epidermal growth factor (EGF), also secreted into their conditioned media substances which competed binding to EGF receptors. Support for this concept of "autocrine" secretion (1,2) was provided by the discovery of acid-stable, heat-stable peptides, called sarcoma growth factor in the conditioned media of Moloney Sarcoma virus transformed cells (3). Sarcoma growth factor not only had the property of binding to the EGF receptor but could also induce the reversible transformation of rat kidney fibroblasts (NRK). This anchorage independent growth in soft agar is now accepted as the operational definition of transforming growth factor (TGF).

Peptides representing two distinct classes of TGF'S have been purified to homogeneity. TGFα and TGF-β are distinguished biochemically by their unique amino acid sequences and biologically by their different activities on cells. TGFα is a single polypeptide chain of 50 amino acids containing three disulfide bonds. TGF-β is a homodimeric structure consisting of two chains of 112 amino acids, each containing nine cysteine residues. The ability to induce anchorage independent growth of NRK cells requires the combined action of TGFα and TGF-β (4).

TGFα is a 6-kd protein which binds to the EGF receptor (5). TGFα shares 33% sequence homology with EGF and has an affinity for the EGF receptor similar to EGF (6). Derynck et al. (7) have shown that TGFα is synthesized as a larger precursor of 160 amino acids. The larger precursor protein is glycosylated and palmitoylated and is thought to be a transmembrane protein that sequentially undergoes external proteolytic cleavage, releasing TGFα species ranging in molecular weight from 6 kd to 25 kd (8).

Examination of a wide variety of human tumors by northern hybridization indicates that squamous, renal, mammary carcinomas as well as melanoma synthesize TGFα mRNA (9). TGFα has also been detected in the urine of cancer patients (10-13) but is also expressed in both fetal and normal tissues. In the mouse embryo TGFα mRNA expression peaks at day 9 and quickly levels off by day 21 (14). TGFα has been detected in human keratinocytes, in bovine anterior pituitary and bovine ovarian theca-interstitial cells (15-18). The function of TGFα in normal cells is presently not known.

It has been suggested that tumor and fetal derived EGF-like peptides are structurally related to TGFα while normal cells produce growth factors related to EGF(1,2). In many cases biological assays have been used to detect the presence of TGFα; however, because of their similarities, biological assays cannot be used to distinguish TGFα from EGF. Currently, there are a limited number of monoclonal antibodies which have been made against TGFα (8,18,19). We have also produced a series of monoclonal antibodies specific for TGFα which do not crossreact with EGF. We have used these antibodies to: specifically detect TGFα in conditioned media of tumor cells; 2) detect TGFα in the urine of cancer patients using a TGFα immunometric assay and by immunoblotting; 3) and to identify TGFα in tumor cells and paraffin-embedded tissues by immunohistological staining.

SUMMARY OF THE INVENTION

The present invention provides a monoclonal antibody which specifically forms a complex with TGFα in formalin-fixed, paraffin-embedded tissue sections which has an affinity of a least $10^7$, and which is directed to the epitope to which monoclonal antibody 213-4.4 (ATCC No. HB9992) is directed. The invention further provides the above-described monoclonal antibody wherein the epitope consists essentially of amino acids 34-43 of TGFα.

Additionally, the present invention concerns the monoclonal antibody 213-4.4 (ATCC NO. HB9992).

The invention also provides a method of detecting TGFα in tissue sections of a tissue in which normal tissue is characterized by the absence of TGFα and neoplastic tissue is characterized by the presence of TGFα in a subset of such neoplastic tissue which comprises contacting the tissue sections with an antibody directed to an epitope on TGFα under conditions such that the antibody binds to the tissue sections detecting the antibody bound to the tissue sections and thereby detecting TGFα in the tissue sections.

The invention further provides the monoclonal antibody 134A-2B3 (ATCC No. HB9993). Additionally, the invention concerns the monoclonal antibody 137-178 (ATCC No. HB9994).

DETAILED DESCRIPTION OF THE INVENTION

Figure 1:
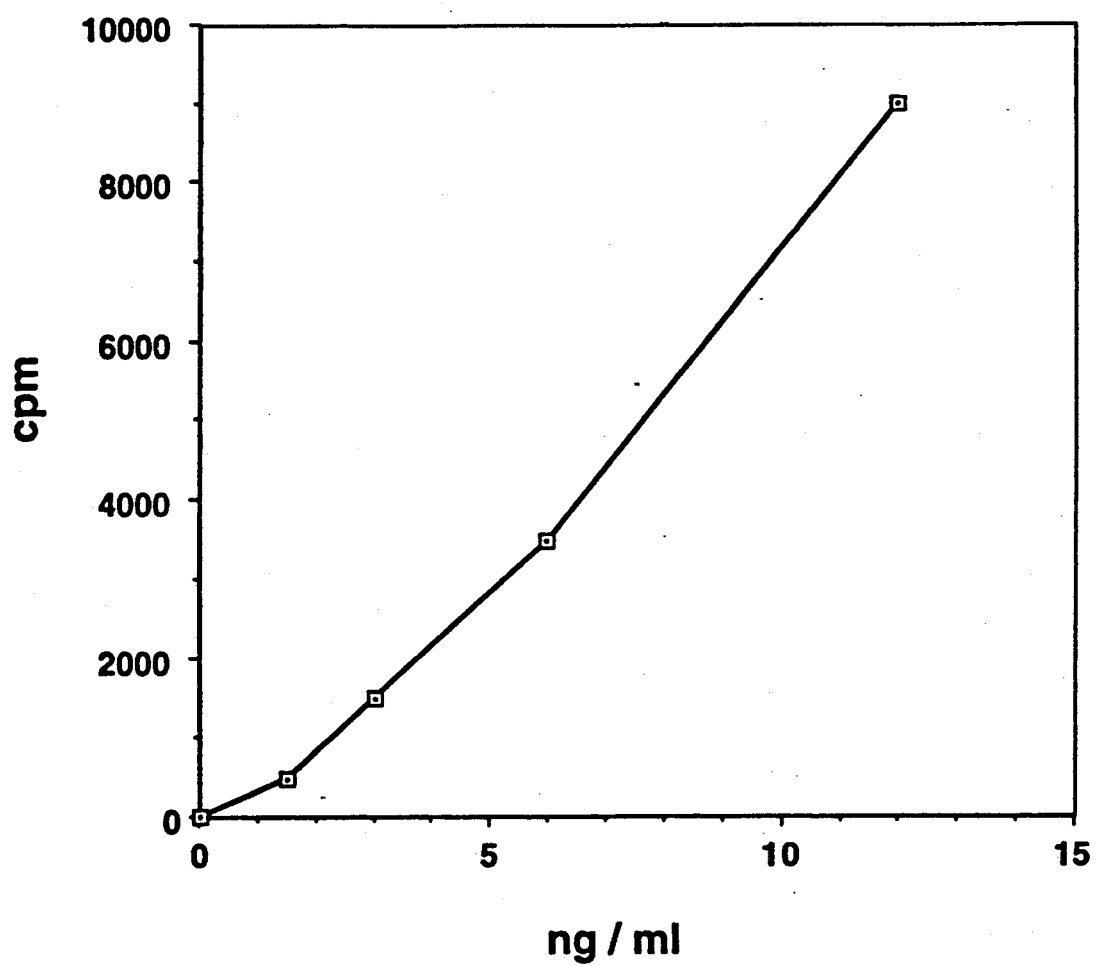
FIG. 1 is the result of a two site immunoradiometric assay for TGFα. The assay was performed in triplicate.

The present invention provides a monoclonal antibody which specifically forms a complex with TGFα in formalin-fixed, paraffin-embedded tissue sections, which has an affinity of at least 107, and which is directed to the epitope to which monoclonal antibody 213-4.4 (ATCC No. HB9992) is directed.

The invention also provides a monoclonal antibody which specifically forms a complex with TGFα in formalin-fixed, paraffin-embedded tissue sections, which has an affinity of at least 107, and which is directed to the epitope to which monoclonal antibody 213-4.4 (ATCC No. HB9992) is directed wherein the epitope consists essentially of amino acids 34-43 of TGFα.

This invention further provides the monoclonal antibody 213-4.4 (ATCC No. HB9992).

Additionally, in one embodiment of the invention the monoclonal antibody which specifically forms a complex with TGFα in formalin-fixed, paraffin-embedded tissue sections, which has an affinity of at least $10^7$, and which is directed to the epitope to which monoclonal antibody 213-4.4 (ATCC No. HB9992) is directed is labeled with a detectable marker. Examples of suitable detectable markers include an enzyme, a paramagnetic isotope, biotin, a fluorophore, a chromophore, a heavy metal, or a radioisotope.

The present invention further concerns a method of detecting TGFα in formalin-fixed, paraffin-embedded tissue sections which comprises contacting the tissue sections with (1) the monoclonal antibody which specifically forms a complex with TGFα in formalin-fixed, paraffin-embedded tissue sections, which has an affinity of at least $10^7$, and which is directed to the epitope to which monoclonal antibody 213-4.4 (ATCC No. HB9992) is directed; (2) the above-described antibody wherein the epitope consists essentially of amino acids 34-43 of TGFα; or (3) the monoclonal antibody 213-4.4 (ATCC No. HB9992) under conditions such that the antibody binds to the tissue sections and detecting the antibody bound to the tissue sections and thereby detecting TGFα in the tissue sections.

Additionally, this invention concerns the above-described method of detecting TGFα in formalin-fixed, paraffin-embedded tissue sections wherein the tissue sections are of a tissue in which normal tissue is characterized by the absence of TGFα and neoplastic tissue is characterized by the presence of TGFα in a subset of such neoplastic tissue. Examples of normal tissues include breast and skeletal muscle tissues and examples of neoplastic tissues include breast carcinomas and myogenic tumors.

A further embodiment of the invention provides the above-described method of detecting TGFα in formalin-fixed, paraffin-embedded tissue sections wherein the monoclonal antibody is labeled with a detectable marker. Examples of suitable markers include an enzyme, biotin, a fluorophore, a chromophore, a heavy metal, a paramagnetic isotope, or a radioisotope.

Another embodiment of the invention provides the above-identified method of detecting TGFα in formalin-fixed, paraffin-embedded tissue sections wherein the monoclonal antibody bound to the tissue sections is detected by contacting the monoclonal antibody with a second antibody which is labeled with a detectable marker under conditions such that the second antibody binds to the monoclonal antibody and detecting the second antibody so bound.

A further embodiment of the invention provides a method of detecting TGFα in tissue sections of a tissue in which normal tissue is characterized by the absence of TGFα and neoplastic tissue is characterized by the presence of TGFα in a subset of such neoplastic tissue which comprises contacting the tissue sections with an antibody directed to an epitope on TGFα under conditions such that the antibody binds to the tissue sections and detecting antibody bound to the tissue, and thereby detecting TGFα in the tissue sections.

Examples of tissue sections include breast and muscle tissues.

Additionally, the invention concerns the above-described method of detecting TGFα wherein (1) the antibody is the monoclonal antibody 213-4.4; (2) the antibody is directed to the epitope to which monoclonal antibody 213-4.4 (ATCC No. HB9992) is directed; and (3) the monoclonal antibody is produced by the hybridoma 213-4.4 (ATCC No. HB9992).

In a further embodiment of the above-described method of detecting TGFα in tissue sections the tissue is formalin-fixed, paraffin-embedded and in another embodiment, the tissue is frozen.

This invention further concerns a method of determining a difference in the amount and distribution of TGFα in tissue sections from a neoplastic tissue to be tested relative to the amount and distribution of TGFα in tissue sections from a normal tissue which comprises contacting both the tissue to be tested and the normal tissue with (1) the monoclonal antibody which specifically forms a complex with TGFα in formalin-fixed, paraffin-embedded tissue sections, which has an affinity of at least $10^7$, and which is directed to the epitope to which monoclonal antibody 213-4.4 (ATCC No. HB9992) is directed; (2) the above-described monoclonal antibody wherein the epitope consists essentially of amino acids 34-43 of TGFα; or (3) the monoclonal antibody 213-4.4 (ATCC No. HB9992) and thereby detecting the difference in the amount and distribution of TGFα.

Another embodiment of the invention provides a method of diagnosing a neoplastic or preoplastic condition in a subject which comprises obtaining from the subject a sample of a tissue, detecting TGFα in such tissue sections using the above-described method of determining a difference in the amount and distribution of TGFα in tissue sections from a neoplastic tissue to be tested relative to the amount and distribution of TGFα in tissue sections from a normal tissue and thereby diagnosing such neoplastic or preoplastic condition.

This invention further provides a method of diagnosing a neoplastic or preoplastic condition in a subject which comprises obtaining from the subject a sample of a tissue, preparing tissue sections from that tissue, detecting TGFα in such tissue sections using the above-described method of detecting TGFα in tissue sections of a tissue in which normal tissue is characterized by the absence of TGFα and neoplastic tissue is characterized by the presence TGFα in a subset of such neoplastic tissue, and thereby diagnosing such neoplastic or preoplastic condition.

In further embodiments of the above-described methods of diagnosing a neoplastic or preoplastic condition in a subject, the antibody is directed to the epitope to which monoclonal antibody 213-4.4 (ATCC No. HB9992) is directed. The invention further includes the above-described methods of diagnosing a neoplastic or preoplastic condition in a subject wherein the tissue sections are breast and muscle tissues.

Additionally, the invention concerning a monoclonal antibody which preferably forms a complex with denatured TGFα and which is directed to the epitope to which monoclonal antibody 134A-2B3 (ATCC No. HB9993) is directed.

Further, this invention concerns the monoclonal antibody 134A-2B3 (ATCC No. HB9993)

In one embodiment of the invention the monoclonal antibody 134A-2B3 (ATCC No. HB9993) is labeled with a detectable marker. Examples of suitable detectable markers include an enzyme, biotin, a heavy metal, a paramagnetic isotope, a fluorphore, a chromophore, or a radioisotope.

Additionally, this invention provides a method of detecting denatured TGFα in a sample which comprises contacting the sample with any of the labelled monoclonal antibodies which preferably forms a complex with denatured TGFα and which is directed to the epitope to which monoclonal antibody 134-2B3 (ATCC No. HB9993) is directed on the monoclonal antibody 134-2B3 (ATCC No. HB9993) such that the TGFα binds to the monoclonal antibody and forms a complex therewith; and detecting such complex.

A further embodiment of the invention provides the above-described method of detecting denatured TGFα in a sample wherein the sample containing denatured TGFα is transfered onto a suitable support under conditions permitting denatured TGFα in the sample to attach to the support prior to contacting the sample with labelled antibody.

Additionally, in another embodiment of the invention the above-described method includes the monoclonal antibody directed to the epitope to which monoclonal antibody 134-2B3 (ATCC No. HB9993) is directed. Further, in still another embodiment of the above-described method of detecting denatured TGFα in a sample the sample includes serum, urine, blood, tissue extracts and phlegm.

This invention also concerns a method of diagnosing a neoplastic or preneoplastic condition in a subject which comprises obtaining from the subject a volume of biological fluid and detecting TGFα in such bodily fluid using the above-described method of detecting denatured TGFα in a sample; thereby diagnosing such neoplastic or preneoplastic condition.

Additionally, this invention concerns the monoclonal antibody 137-178 (ATCC No. HB9994). In one embodiment of the invention the monoclonal antibody 137-178 (ATCC No. HB9994) is labeled with a detectable marker. Examples of suitable markers include an enzyme, biotin, a fluorophore, a chromophore, a heavy metal, a paramagnetic isotope, or a radioisotope.

The present invention further concerns a method of detecting TGFα in a biological fluid sample which comprises (a) contacting a solid support with an excess of (1) a monoclonal antibody which specifically forms a complex with TGFα in formalin-fixed, paraffin-embedded tissue sections, which has an affinity of at least $10^7$, and which is directed to the epitope to which monoclonal antibody 213-4.4 (ATCC No. HB9992) is directed; (2) a monoclonal antibody which preferably forms a complex with denatured TGFα and which is directed to the epitope to which monoclonal antibody 134A-2B3 (ATCC No. HB9993) is directed; or (3) the monoclonal antibody 137-178 (ATCC No. HB9994) under conditions permitting the monoclonal antibody to attach to the surface of a solid support; (b) contacting the resulting solid support to which the monoclonal antibody is bound with a biological fluid sample under conditions such that the TGFα in the biological fluid binds to the antibody and forms a complex therewith; (c) contacting the complex formed in step (b) with a predetermined amount of a second antibody labeled with a detectable marker and directed to an epitope on TGFα different from the epitope to which the monoclonal antibodies of step (a) is directed, so as to form a complex which includes TGFα, the monoclonal antibody, and the second detectable antibody; (d) detecting and quantitatively determining the concentration of second detectable antibody present in the complex formed in step (c); and (e) thereby detecting and quantitatively determining the concentration of TGFα in the biological fluid sample.

In one embodiment of the above-described method of detecting and quantitatively determining the concentration of TGFα in a biological fluid sample the antibody bound to the solid support is directed to the epitope to which monoclonal antibody 137-178 (ATCC No. HB9994) is directed.

In another embodiment of the above-described method of detecting and quantitatively determining the concentration of TGFα in a biological fluid sample the second antibody is directed to the epitope to which monoclonal antibody 134-2B3 (ATCC No. HB9993) is directed.

Examples of biological fluids include tissue extract, urine, blood, serum, and phlegm.

Examples of suitable markers include an enzyme, biotin, a fluorophore, a chromophore, a heavy metal, a paramagnetic isotope, or a radioisotope.

This invention also concerns a method of diagnosing a neoplastic or preneoplastic condition in a human being which comprise obtaining from the subject a sample of biological fluid using the above-described method of detecting and quantitatively determining the concentration TGFα in a biological fluid sample and thereby diagnosing such neoplastic or preneoplastic condition.

The present invention further provides a method of treating a subject, such as a human being, with a neoplastic or preneoplastic condition which comprises administering, for example, by intravenous administration, to the subject an effective amount of a (1) monoclonal antibody which specifically forms a complex with TGFα in formalin-fixed, paraffin-embedded tissue sections, which have an affinity of at least $10^7$, and which is directed to the epitope to which monoclonal antibody 213-4.4 (ATCC No. HB9992) is directed; (2) a monoclonal antibody which preferably forms a complex with denatured TGFα and which is directed to the epitope to which monoclonal antibody 134-2B3 (ATCC No. HB9993) is directed; or (3) the monoclonal antibody 137-178 (ATCC No. HB9994) and a pharmaceutically acceptable carrier.

Additionally, the invention concerns a method of treating a subject, such as a human being, for psoriasis which comprises administering, for example, by topical application to the subject, an effective amount of (1) a monoclonal antibody which specifically forms a complex with TGFα in formalin-fixed, paraffin-embedded tissue sections, which has an affinity of at least $10^7$, and which is directed to the epitope to which monoclonal antibody 213-4.4 (ATCC No. HB9992) is directed; (2) monoclonal antibody which preferably forms a complex with denatured TGFα and which is directed to the epitope to which monoclonal antibody 134A-2B3 (ATCC No. HB9993) is directed; or (3) the monoclonal antibody 137-178 (ATCC No. HB9994) and a pharmaceutically acceptable carrier.

This present invention further provides a method of inhibiting the proliferation of cells which comprises treating the cells with an amount of (1) the monoclonal antibody which specifically forms a complex with TGFα in formalin-fixed, paraffin-embedded tissue sections, which has an affinity of at least $10^7$, and which is directed to the epitope to which monoclonal antibody 213-4.4 (ATCC No. HB9992) is directed; (2) a monoclonal antibody which preferably forms a complex with denatured TGFα and which is directed to the epitope to which monoclonal antibody 134A-2B3 (ATCC No. HB9993) is directed; or (3) the monoclonal antibody 137-178 (ATCC No. HB9994).

Additionally, the invention provides a method of inhibiting the biological activity of TGFα which comprises contacting TGFα with an amount of (1) the monoclonal antibody which specifically forms a complex with TGFα and formalin-fixed, paraffin-embedded tissue sections, which has an affinity of at least $10^7$, and which is directed to the epitope to which monoclonal antibody 213-4.4 (ATCC No. HB9992) is directed; (2) a monoclonal antibody which preferably forms a complex with denatured TGFα and which is directed to the epitope to which monoclonal antibody 134A-2B3 (ATCC No. HB9993) is directed; or (3) the monoclonal antibody 137-178 (ATCC No. HB9994) effective to inhibit the activity of TGFα.

The invention further provides a composition which comprises one of the above-described monoclonal antibodies to which an imaging agent is attached.

Methods for attaching an imaging agent to a monoclonal antibody are, of course, well known to those skilled in the art.

Examples of suitable imaging agents include a paramagnetic isotope, a heavy metal, or a radioisotope.

This invention further provides the method of imaging a neoplastic or preneoplastic cell type which comprises contacting the tumor cells with the above-mentioned composition under condition such that the composition preferentially binds to the neoplastic or preneoplastic cells and detecting the composition so bound to the neoplastic or the preneoplastic cells.

Additionally, the invention provides a therapeutic composition which comprises (1) a monoclonal antibody which specifically forms a complex with TGFα in formalin-fixed, paraffin-embedded tissue sections, which have an affinity of $10^7$, and which is directed to the epitope to which monoclonal antibody 213-4.4 (ATCC No. HB9992) is directed; (2) monoclonal antibody which preferably forms a complex with denatured TGFα and which is direct to the epitope to which monoclonal antibody 134A-2B3 (ATCC No. HB9993) is directed; or (3) the monoclonal antibody 137-178 (ATCC No. HB9994) to which a therapeutic agent is attached.

Examples of therapeutic agents include ricin diphtheria toxin, pseudomonas, exotoxin-A, abrin, supporin, and gelnoin, as well as conventional therapeutic drugs.

Finally, this invention provides a therapeutic method which comprises administering to a subject an effective amount of the above-described therapeutic composition.

MATERIALS AND METHODS

Synthetic TGFα Antigen

The primary amino acid sequence of human TGFα was obtained from the sequence deduced by the cDNA cloning of TGFα (7). The synthesis of TGFα (1-50) and TGFα (34-50) peptide was performed by the solid-phase method as described previously by Tam et al (20). The TGFα (35-50) peptide was coupled to KLH as previously described (20). The TGFα (34-43) peptide used for epitope analysis was purchased for Bachem Inc. (CA).

Recombinant TGFα Antigen

The gene encoding for the processed form of human TGFα was produced using phosphoramidite chemistry. The nucleotide sequence was optimized for condon usage in E. coli and the gene was produced by the ligation of synthetic oligonucleotides. The synthetic gene was then fused to a segment of E. coli trpE gene carried in an expression plasmid vector for the production of the protein in bacterial cells. The fusion protein expressed from the PKS-TGFα plasmid constitutes a major protein in the bacterial lysate. The trpE::TGFα fusion protein (10 kd) was purified by gel filtration on Sephadex G-75 in 4M guanidine-hydrochloride as described by Winkler et al (20). The purified trpE::TGFα protein was refolded by air oxidation in the presence of glutathione and treated with CNBr to release mature (6 kd) TGFα. The 6 kd TGFα was purified by HPLC on Waters C-18-u Bondpack reverse phase column as previously described (22). The 6Kd protein was biologically active and confirmed to be the TGFα by amino acid analyses and N-terminal sequencing.

Single base changes were made in the DNA sequence for human TGFα at amino acid positions Cys 8, Cys 16, Cys 32, Cys 43 by oligonucleotide synthesis of DNA fragments encoding TGFα proteins containing the following changes: Mutant I (Cys 8→Ser 8), Mutant II (Cys 16→Ser 16), Mutant VI (Cys 32→Phe 32) and Mutant IV (Cys 43→Ser 43). The proteins were expressed as trpE fusion proteins and purified as described above.

Monoclonal Antibody Production

Young BALB/c mice (3 to 5 weeks) were immunized by subcutaneous injection of 20 μg of either TGFα (34-50)-KLH conjugate, TGFα (1-50) or recombinant TGFα. Seven days later the mice were boosted with polystyrene beads coated with antigen. Thirty days later mice were injected intravenously with 20 μg antigen. Three days later the mice were sacrificed by cervical dislocation, spleens removed, and spleen cells were isolated by teasing the spleen apart in RPMI 1640 media (M.A. Bioproducts, Walkersville, Md.). Erythrocytes were lysed by treatment with 0.17M ammonium chloride, and the spleen cells were counted in a hemocytometer. Fusions were conducted using a ratio of four spleen cells to one myeloma cell Ag 8.653 which does not express heavy or light chains of immunoglobulin before hybridoma formation. Cells were centrifuged 200 g for 5 minutes and resuspended in 35% polyethylene glycol, 1300–1600 molecular weight (ATCC, Rockville, Md.) and centrifuged 200 g for 6 minutes. The fused cell pellet was suspended in RPMI 1640 supplemented with 20% fetal bovine sera (Hyclone Laboratories) 1.0 mM sodium pyruvate, and 10% HCTC 109 medium (MA Bioproducts) and cultured in a T150 flask at 37° C. in a humidified 10% $CO_2$—90% air incubator overnight. The following day the media was supplemented with $1 \times 10^{-7}$M aminopterin, and $1.6 \times 10^{-5}$M thymidine and plated in microtiter plates (Costar, Cambridge, Mass.) at a concentration of $1.0 \times 10^6$ cells per well. After 10 to 12 days of incubation at 37° C., culture fluids from wells containing actively growing hybrid colonies were harvested and screened.

Primary Hybridoma Screen

Elisa plates (Dynatech) were coated for 16 hours at 4° C. with 25 ng per well of TGFα (34-50) peptide, recombinant TGFα or synthetic TGFα in PBS. All the following incubations were performed at room temperature. The plates were rinsed with PBS-0.05% Tween 20 (PBS-Tween) and blocked with PBS-1% BSA-0.02% NaN$_3$ for 1 hr. The wells were incubated with 1:5 dilution of hybridoma supernatant for 1 hr, washed three times and incubated with alkaline phosphatase-conjugated goat anti-mouse IgG in PBS-Tween for one hour. The plates were again washed three times and incubated with p-nitrophenyl phospate (1 mg/ml) in diethanolamine pH 9.0 containing MgCl$_2$, 0.02% % NaN$_3$ for 30 min. The absorbance was measured at 412 nm using a Dynatech multiscan autoreader.

Secondary Hybridoma Screens

A screen was developed to epitope map the hybridoma supernatants generated from spleens of mice immunized with synthetic TGFα using the Pandex screen machine. Polystyrene beads were coated with rabbit anti-TGFα (34-50) IgG in 0.1 ml NaHCO$_3$ pH 9.0 overnight at 4° C. The beads were washed with PBS and blocked with PBS-BSA at 4° C. overnight. Ten μl of beads were incubated with synthetic TGFα (500 ng) for 30 minutes at room temperature. After washing with PBS-BSA the plates were incubated with a 1:5 dilution of a hybridoma supernatant for 30 minutes at room temperature. The beads were washed and incubated with fluorescein-conjugated goat anti-mouse IgG for 30 min washed three times and the fluorescein read at 485/535 nm.

An additional assay was developed to screen hybridomas generated from mice immunized with recombinant trpE-TGFα fusion protein. Ninety-six well polystyrene plates were incubated with 50 μl/well of PBS containing 1 μg of goat anti-mouse IgG (Cappel) overnight at 4° C. The plates were washed with PBS-Tween and nonspecific sites on the plastic were blocked with PBS-BSA for 1 hour. After washing with PBS-Tween the wells were incubated with 1:5 dilution of hybridoma supernatant for 1 hr at room temperature. The plates were washed three times with PBS-Tween and free goat anti-mouse IgG sites were blocked with 1% normal mouse sera in PBS-BSA for 1 hour at 37° C. and washed. Fifty nanograms of trpE-TGFα fusion protein (10 kd) was added for 1 hour and the wells were washed. One μg of biotin-123-278 IgG was added to the plates for one hour and washed. Antibody 128-278 is a mouse monoclonal antibody which reacts specifically with the trpE protein in the trpE-TGFα fusion protein and not TGFα. Antibody 278 was conjugated to biotin (BRL) according to the manufacturer's instructions. Strepavidin conjugated-alkaline phosphatase (Fisher) was added for one hour and the plates were washed four times with PBS-Tween. p-Nitrophenyl phosphate (1 mg/ml) in diethanolamine pH 9.0 containing MgCl$_2$, and 0.02% NaN$_3$ was added for 30 minutes and the absorbance was measured at 412 nm. Hybridomas producing TGFα antibody were subcloned twice by limiting dilution.

Ascites production and purification of immunoglobulin

Clones selected for immunoglobulin purification were grown in syngeneic mice as ascitic tumors. Hybridoma cells ($3.0 \times 10^7$) were cultured for 2 hrs in serum-free culture medium and injected into the peritoneal cavity of pristane-treated Balb/c mice. Ascites fluid was harvested within 7 to 10 days and clarified by centrifugation at $2,500 \times g$ for 10 min. IgG was purified by ammonium sulfate precipitation and ion exchange chromatography using Waters HPLC instrumentation.

Isotyping of Immunoglobulin 96 well polystyrene mictotiter assay plates were coated overnight at 4° C. for 3 hours at 37° C. with 50 μl/well of 0.1M NaHCO$_3$, pH 9.0, containing 50 ng of TGFα. After rinsing twice with PBSTween 150 μl/well of PBS-1% BSA was added and blocking proceeded for 1 hour at room temperature before rinsing twice with PBST. 50 μl/well of 8 isotyping reagents (Southern Biotechnology, Birmingham, Ala.) was added at a dilution of 1/500 in PBS-0.1% BSA and incubated 1 hour at room temperature. The wells were then washed 6 times with PBSTween and 50 μl/well of substrate solution added. After 15 min. the reaction was stopped with 50 μl/well of 3M NaOH and the absorbance at 405 nm determined.

Biological Assays for EGF and TGFα

The binding competition of EGF and TGFα for the EGF receptor was measured in a solid-phase radioreceptor assay using $^{125}$I-labeled murine EGF (Amersham) and membranes prepared from A431 epidermoid carcinoma as previously described (13). The induction of colony formation in soft agar was assayed using NRK cells, clone 49F as previously described (4).

Chromatography

Gel filtration chromatography was performed on Bio-Gel P-10 or P-60 (Bio-Rad) equilibrated in 1M acetic acid. High pressure liquid chromatography (HPLC) was performed on Waters Associated C-18-U Bondpack reverse-phase column using a linear gradient from 0-60% acetonitrile in 0.05% trifluoroacetic acid over 60 minutes. The flow rate was 1 ml/min and 3 ml fraction were collected.

Isolation of TGFα from Human Urine and Conditioned Media

All samples were brought to a final concentration of 1 mM phenylmethylsulfonylfluoride (PMSF, Sigma Chem) and dialyzed at 4° C. against 1M acetic acid—0.5 mM PMSF using 3.5 kd cutoff dialysis tubing (Spectrum Industries). After extensive dialysis, the samples were clarified and lyophilized. Lyophilized protein from twenty-four hour urine samples (500 ml-2000 ml) or conditioned media (500-1000 ml) were subjected to Bio Gel P-10 or P-60 chromatography. Aliquots of every other fraction were tested in the EGF receptor competition assay and fractions containing activity were pooled and lyophilized. The pools were resuspended in SDS-PAGE sample buffer and tested by immunoblotting. TGFα was partially purified from conditioned serum-free media of A375 melanoma cells and FeSV rat cells exactly as described above.

Immunoblotting Analysis

Samples to be analyzed were first subjected to SDS-PAGE on 15% acrylamide gels as described by Laemmli (23). After electrophoresis, transfer of proteins to nitrocellulose (Schleicher & Schuell, BA 85, 0.45 um) was performed as described by Towbin et al. (24). Proteins were transferred at 70 volts for 2-3 hours at 4° C. The nitrocellulose was incubated in 0.5% non-fat powdered milk (Carnation) in 10 mM Sodium Phosphate—200 mM NaCl pH 7.4 (PBS) containing 0.2% sodium azide for 1 hour at room temperature. The filter was then washed with PBS-Tween and incubated with TGFα monoclonal antibodies (10 μg/ml) diluted in the same buffer for 2 hours at room temperature. After washing three times with PBS-Tween, filters were incubated with a 1:500 dilution of affinity purified rabbit anti-mouse IgG (Cappel) for 1 hour and washed. $^{125}$I-labeled protein A ($2 \times 10^6$ cpm/50 ml PBS-Tween) was added for 45 minutes at room temperature. The filters were washed three times with PBS-Tween-20, dried and exposed to Kodak XAR-5 film—at 70° C. using intensifying screens.

Development of Immunoradiometric assay for TGFα

Star tubes (12×75 mm, Nunc) were coated with 3 ug of 137-178 IgG in 0.5 ml of 0.1M NaHCO$_3$ pH 9.1 at 4° C. overnight. The tubes were washed with PBS and 1 ml of PBS-1%BSA-0.02%—NaN$_3$ was added for one hour at room temperature to block nonspecific sites on the plastic.

The tubes were washed and incubated with 0.5ml of PBS-BSA containing dilutions of TGFα or test sample and 200,000 cpm (1.5 ng) of $^{125}$I-134A-2B3 IgG for 3 hours at room temperature with shaking. The tubes were washed three times with PBS, once with PBS containing 0.1% Triton x-100 and counted in a LKB RIA gamma counter (LKB). TGFα concentrations in the test samples were calculated from a standard curve of TGFα. All assays were performed in triplicate.

Immunohistological Staining of Tumor Cells

A375 melanoma cells and Snyder-Theilen sarcoma virus-transformed Fischer rat embryo cells (FeSV) were obtained from American Type Culture Collection (ATCC, Md.). Cells were cultured in Dulbecco's Modified Eagle's Medium (DMEM) containing 10% fetal calf serum in Lab Tek plates. For immunofluorescence studies, cells were rinsed in phosphate-buffered saline (PBS) and fixed in 100% ice cold methanol for 10 minutes. The cells were then incubated with monoclonal antibody (20 μg/ml) in PBS containing 2% BSA for one hour at room temperature, washed in PBS, and air dried for 30 minutes. The slides were wet with PBS, incubated with 25μg/ml of rhodamine conjugated-goat anti-mouse IgG (Cappel Labs) for 45 minutes, and washed again with PBS. After mounting coverslips with 90% glycerol the cells were examined by epifluorescence using a Leitz Orthoplan 2 scope. Formalin-fixed, paraffin embedded tissues sections (5–7 μm) were obtained from Carolina Biological Supply Co. (N. Carolina). The sections were deparaffinized by extraction in xylene. They were rehydrated by treatment with graded alcohols and distilled water. Sections were treated with 0.1% H$_2$O$_2$ for 30 minutes to consume endogenous peroxidase activity, and with 5% normal goat serum (Cappel Laboratories) for 20 minutes to suppress non-specific antibody binding. Paired sections on each slide were incubated with purified monoclonal antibody (20 μg/1 ml) or a control mouse IgG for 18 hours. Bound antibody was detected by sequential incubation with biotinylated goat antibody mouse IgG for 30 minutes, with avidin DH-biotinylated horseradish peroxidase H complexes (Vector Laboratories, Burlingame, Calif.) for 30 minutes, and with 0.2% 3,3,-diaminobenzidene tetrahydrochloride (Sigma Chemicals, St. Louis, Mo.) plus 0.001% H for approximately 5 minutes, to yield a brown reaction product. The preparations were counterstained with hematoxylin, mounted with Permount and examined by light microscopy.

The specificity of immunostaining was verified by absorption of monoclonal antibodies with TGFα or EGF for 30 min at room temperature prior to incubation with tissues or cells.

Results

Characteristics of TGFα Monoclonal Antibodies

Table 1 shows the monoclonal antibodies produced using various immunogens. The antibodies described are representative of many hybridomas selected from a large number of fusions from mice immunized with the three different antigens. The remaining clones from these fusions along with hybridomas from fusions not listed in Table I were frozen. None of the antibodies showed crossreactivity with human EGF as determined by immunoblotting.

Two screening assays were developed to select clones from splenic fusions of mice immunized with synthetic or recombinant TGFα. The screen for hybridoma supernatants generated from synthetic TGFα was useful for the selection of antibodies which did not react with the 34-50 epitope. This is important since it is known that the 34-50 peptide is an immunodominant epitope on TGFα (18,21). The assay uses a polyclonal rabbit anti-TGFα (34-50) to capture the antigen and then specifically selects hybridoma secreting antibodies to other epitopes.

A second assay was developed to screen for antibodies made against recombinant trpE-TGFα fusion protein. This assay utilizes the trpE-TGFα fusion protein as antigen which easily purified from E. coli containing the recombinant trpE-TGFα gene. The assay is especially useful for the selection of antibodies which can specifically capture TGFα.

The antigen is then detected using a monoclonal antibody to the trpE segment of the trpE-TGFα fusion protein. Antibodies which react with the trpE segment of the fusion protein are eliminated by double screening with a different trpE fusion protein, e.g., trpE-H-ras. Antibodies reacting with only trpE-TGFα and not trpE-H-ras are saved while those reacting with both trpE-TGFα and trpE-H-ras (or only trpE-H-ras alone) are discarded. An example of this is shown in Table II. For example, antibody 208-13H9 would be discarded since it reacts with both trpE-TGFα and trpE-H-ras. The specificity of this assay is demonstrated by using a capture antibody specific for H-ras. (Table II). This assay could potentially be used for screening monoclonal antibodies against any recombinant fusion protein. In addition, its use could be extended as a generic screen for the detection of serum antibodies i.e., to determine if human serum contains antibodies to a particular antigen, e.g., AIDS virus, etc.

TABLE I

Characteristics of TGFα monoclonal antibodies.

| Clone | Immunogen | Isotype | $K_a$ (M$^{-1}$) | Blot |
|---|---|---|---|---|
| 134-2B3 | sTGF | IgG$_1$, k | $1 \times 10^8$ | +++ |
| 137-178 | sTGF | " | $2 \times 10^7$ | — |
| 186-290.1 | (34–50) | " | $4 \times 10^6$ | + |
| 186-114.1 | " | " | ND | + |
| 186-897.1 | " | " | $6 \times 10^7$ | + |
| 189-1183.1 | " | " | ND | + |
| 189-1230.2 | rTGF | " | $2 \times 10^8$ | + |
| 189-2130.1 | " | " | $2 \times 10^7$ | + |
| 189-2062.2 | " | " | $3 \times 10^8$ | +++ |
| 189-1540.2 | " | " | $2 \times 10^7$ | + |
| 189-2567 | " | ND | $2 \times 10^8$ | + |
| 208-8E9 | " | IgG2a,2b | ND | — |

TABLE I-continued

| Characteristics of TGFα monoclonal antibodies. | | | | |
|---|---|---|---|---|
| 208-1F11 | " | " | ND | — |
| 208-1705 | " | " | ND | — |
| 213-2.4 | " | ND | ND | + |
| 213-3.11 | " | IgG,2a | $2 \times 10^7$ | + |
| 213-4.4 | " | IgG,2a | $2 \times 10^7$ | + |

| Clone | Histochemistry[b] | EGF Crossreactivity[c] |
|---|---|---|
| 134-2B3 | + | — |
| 137-178 | + | — |
| 186-290.1 | — | — |
| 186-114.1 | — | — |
| 186-897.1 | — | — |
| 189-1183.1 | — | — |
| 189-1230.2 | — | — |
| 189-2130.1 | — | — |
| 189-2062.2 | — | — |
| 189-1540.2 | — | — |
| 189-2567 | — | — |
| 208-8E9 | — | — |
| 208-1F11 | — | — |
| 208-1705 | — | — |
| 213-2.4 | + | — |
| 213-4.4 | + | — |

[a]100ng TGFα
[b]Immunofluorescence and peroxidase staining of paraffin embedded sections
[c]Determined by immunoblotting
ND = Not determined Epitope Analysis of TGFα Monoclonal Antibodies Using TGFα (34-50) and (34-43) peptides as well as the recombinant TGFα mutant proteins, the epitope recognized by the monoclonal antibodies were analyzed. The results are shown in Table III. Antibodies 189-2062.2 and 134A-2B3 react with an epitope on TGFα located near cysteine 16 since these antibodies show no reactivity with a mutant containing serine at this position. Antibodies 213-3.11 and 213-4.4 both react with the TGFα 34-53 peptide, with 231-4.4 showing somewhat better with the 34-43 peptide. Using this analyses antibodies were selected for the development of an immunometric assay as described below.

Development of a Two-Site Immunoradiometric Assay for TGFα

The immunometric assay for TGFα uses 137-178 to capture TGFα and $^{125}$I-134A-2B3 IgG as the detection system. A typical standard curve is shown in FIG. 1. The sensitivity of this assay for biologically active recombinant or synthetic TGFα is 2 ng/ml. The assay shows no cross reactivity with up to 100-fold excess of human EGF (data not shown).

TABLE II

Selection of capture antibodies using fusion proteins as antigens
ELISA ABSORBANCE (412 NM)[a]

| Clone | TrpE::TGFα | TrpE::H-ras |
|---|---|---|
| 208-1F11 | 1.09 | 0.05 |
| 208-8E9 | 0.396 | 0.05 |
| 208-13H9 | 1.02 | 0.27 |
| 208-17D5 | 1.13 | 0.015 |
| 208-27F11 | 0.961 | 0.000 |
| 134A-2B3 | 1.01 | 0.000 |
| 189-2130 | 0.966 | 0.000 |
| 132-62 (H-ras specific) | 0.021 | 0.841 |

[a]Assay performed using 25ng of antigen

TABLE III

Epitope analysis of TGFα Monoclonal Antibodies

| Clone | Epitope 34–43[a] | 34–50[b] | Mutant II (Cys 16 → Ser 16)[c] |
|---|---|---|---|
| 137-178 | — | — | — |
| 134A-2B3 | — | — | ++ |
| 186-290.1 | + | + | — |
| 186-114.1 | + | — | — |
| 186-897.1 | + | + | — |
| 189-1183.1 | — | — | — |
| 189-1230.2 | — | — | — |
| 189-2062.2 | — | — | ++ |
| 189-1540.2 | — | — | — |
| 189-2567 | — | — | — |
| 208-8E9 | ND | ND | ND |
| 208-1705 | " | " | " |
| 213-2.4 | " | " | " |
| 213-3.11 | + | + | — |
| 213-4.4 | ++ | + | — |

Figure 2:
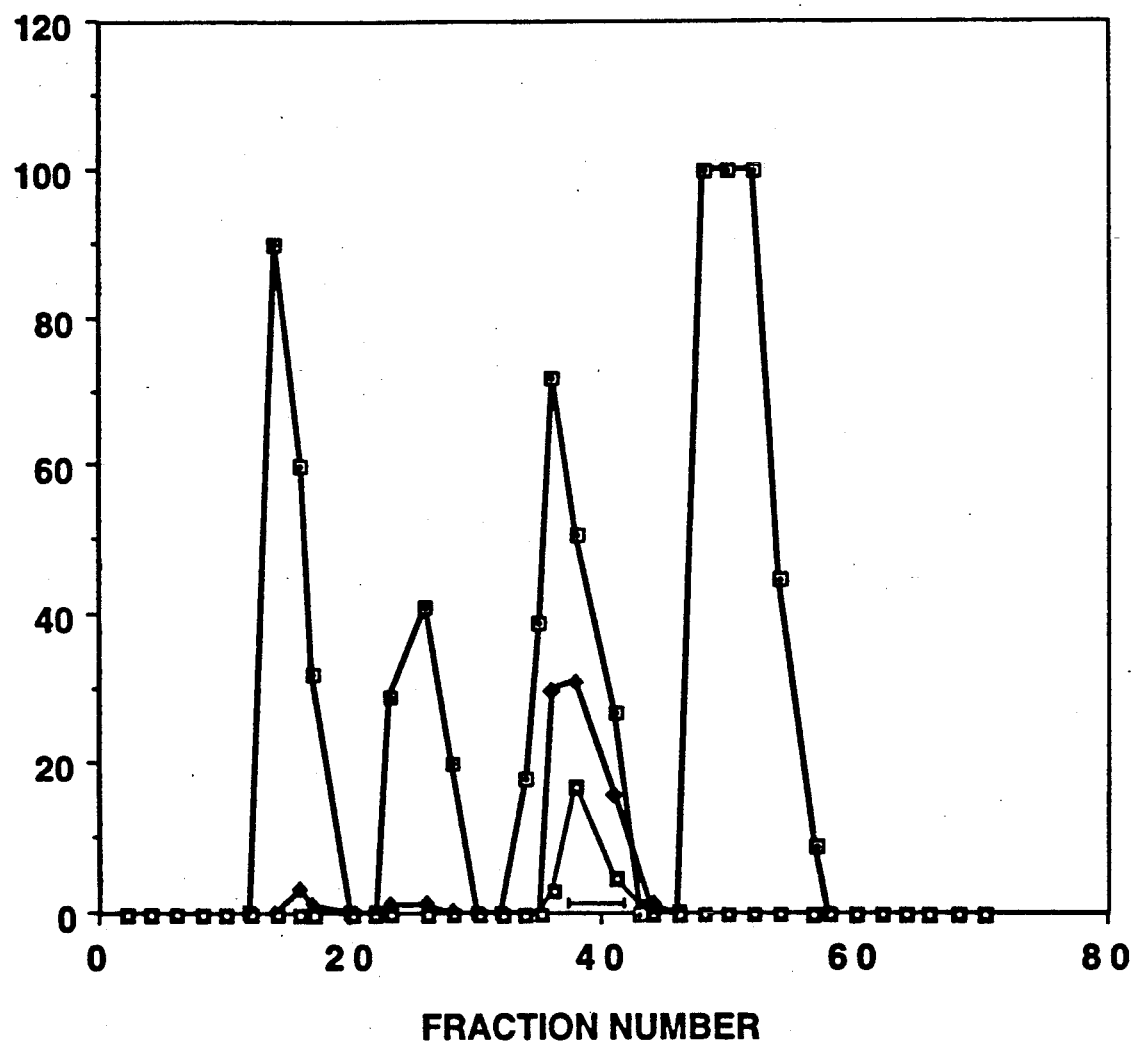
FIG. 2 is a chromatogram of Biogel P-60 chromatography of A375 melanoma cell conditioned media. Fractions were analyzed by the EGF competition binding assay, soft agar assay and TGFα immunoradiometric assay. (□) % of competition of EGF binding; (■) # colonies, 3 Fields>20 cells; (◨) ng/ml TGFα. Fractions active in these three assays were pooled (—).

[a,b]Determined by Elisa using 25ng peptide.
[c]Determined by immunoblotting purified wild type and mutant TGFα
"—" = Not reactive with epitope
"+" = Reactive with epitope
ND = Not determined In order to demonstrate that the test reacts with TGFα isolated from a biological source, TGFα was partially purified from A375 cells. Conditioned media from A375 cells was chromatographed over Biogel P-60 and the fractions were tested in EGF receptor competition, soft agar assay and the TGFα immunoassay. Several peaks of TGFα biological activity were identified but only one peak at $M_r = 8000$ exhibited reactivity in the immunoassay (FIG. 2). These fractions were pooled and the immunoreactive species in the capture test was shown to be TGFα by immunoblotting with 134A-2B3 (data not shown). In addition, the amount of TGFα present in the Biogel P-60 pool by the immunoassay correlated with the amount of TGFα detected in the EGF receptor competition binding assay (Table IV).

TGFα was also detected in condition media of FeSV transformed rat cells. Fractions were assayed in the EGF receptor competition assay and those containing activity were pooled and analyzed by immunoblotting using TGFα monoclonal 134A-2B3 IgG. The antibody reacted with 6 kd TGFα and the 18kd TGFα precursor which has been previously described (25) (data not shown).

TABLE IV

| Quantitation of TGFα from Biogel Pool | |
|---|---|
| ASSAY | ng TGFα/100 ug protein |
| EGF Receptor Competition | 3.12 |
| TGFα Immunometric Assay | 2.8 |
| Soft Agar Assay | +++ |

Immunohistological Staining of Tumor Cells and Tissues

The ability of the antibodies to detect TGFα in tumor cell lines by indirect immunofluorescence was assessed. Using A375 melanoma cells and FeSV transformed rat fibroblasts, or human foreskin fibroblasts (HUF) and Fischer rat embryo cells (FRE) as control, TGFα was detected using 213-4.4 while no staining was detected using an irrelevant antibody control (Table V). The two control cell lines HUF and FRE were negative.

The specificity of the reaction was confirmed by preincubating TGFα monoclonal antibody 213-4.4 with 5μg/1 ml TGFα or EGF prior to its addition to cells. No staining was detected when the antibody was preincubated with TGFα while staining was observed when cells were preincubated with EGF (Table VI). TGFα antibody 213-4.4 was also tested for its ability to react with paraffin-embedded tissues. Table VII shows the distribution of TGFα in normal tissues using TGFα antibody 213-4.4. Preliminary analysis of paraffin-embedded tumor sections shows differences in both the amount and distribution of TGFα when compared with normal tissue.

TABLE V

SUMMARY OF IMMUNOFLUORESCENCE STUDIES WITH TGFα MAbs[1]

| | | REACTIVITY ON CELL LINES[2] | | | |
|---|---|---|---|---|---|
| CLONE | ISOTYPE | A375 | HUF | FeSV/FRE | FRE |
| 137-178 | IgG1, k | ++ | ± | ++ | − |
| 134A-2B3 | " | + | + | − | − |
| 186-290.1 | " | ++ | ++ | NT | NT |
| 186-114.1 | " | ++ | ++ | NT | NT |
| 186-897.1 | " | ++ | ++ | ++ | + |
| 189-1231.2 | " | − | − | − | − |
| 189-2130.1 | " | + | + | + | − |
| 189-2062.2 | " | − | − | − | − |
| 213-2.4 | " | ++ | + | ++ | + |
| 213-3.11 | " | ++ | + | ++ | + |
| 213-4.4 | " | +++ | ± | +++ | ± |
| Control IgG | " | − | − | − | − |

[1]Antibodies tested were those which react with urinary TGFα.
[2]Methanol fixation of cells using 25 μg/ml of antibody.
NT = Not tested

TABLE VI

SPECIFICITY DETERMINATION OF TGFα REACTIVITY

| | Preincubation[1] | | REACTIVITY ON |
|---|---|---|---|
| CLONE | EGF[2] | TGFα | A375 CELLS[2] |
| 213-4.4 | 5 ug/ml | − | +++ |
| 213-4.4 | − | 5 ug/ml | − |
| 213-2.4 | 5 ug/ml | − | ++ |
| 213-2.4 | − | 5 ug/ml | − |
| 213-3.11 | 5 ug/ml | − | ++ |
| 213-3.11 | − | 5 ug/ml | − |
| 137-178 | 5 ug/ml | − | + |
| 137-178 | − | 5 ug/ml | − |

[1]Antibodies were preincubated with EGF or TGFα for 60 minutes at room temperature.
[2]Intensity of staining was identical when cells were preincubated with buffer.
[3]Experiment was performed with methanol fixed cells using 25 ug/ml of antibody.

TABLE VII

TGFα DISTRIBUTION IN NORMAL TISSUES

| TISSUES | TGFα reactivity |
|---|---|
| Kidney | |
| glomerulus | ○ |
| proximal tubule | ⊘ |
| distal tubule | ● |
| collecting tubules | ● |
| Bladder | ● |
| Breast | |
| ductal cells | ⊘ |
| acinar cells | ⊘ |
| Skin | |
| epidermis | ● |
| dermis | ○ |
| Brain | |
| cerebellum | ● |
| Lung | |
| bronchus | ● |
| alveoli | ● |
| Colon | ⊘ |
| Placenta | ● |
| Pancreas | ● |
| Spleen | ○ |
| Thymus | ○ |
| Lymph Node | ○ |
| Testis | ● |
| Ovary | ● |
| Liver | NT |
| Thyroid | NT |
| Adrenal | NT |

● = Positive reactivity
⊘ = Weak reactivity
○ = No reactivity
NT = Not tested

Detection of TGFα in human urine of melanoma patient by immunoblotting

Urine was obtained from a patient with malignant melanoma before and after treatment of disease and was processed by column chromotography as described in Materials and Methods. The pools containing TGFα biological activity were immunoblotted with antibody 134A-2B3. TGFα was detected in the urine sample from the patient prior to treatment whereas no TGFα was found in the patient's urine after treatment of the disease (Table VIII). Analysis of urine from a normal individual by gel filtration and immunoblotting, showed no TGFα (data not shown).

Detection of TGFα in urine the TGFα immunometric assay

TGFα was found to be elevated in the females and cancer patients. One liter urine samples from cancer patients, females in the first trimester of pregnancy or normal controls were processed as described above. The pools containing TGFα bioactivity were tested in the TGFα immunometric assay. Urine from pregnant females was found to be positive when compared with urine from normal individuals. Urine from some cancer patients showed slight elevation of TGFα as compared to normals (data not shown).

TABLE VIII

Immunoblotting of TGFα from urine of melanoma patient before and after treatment[a]

| | EGF receptor assay | Immunoblot |
|---|---|---|
| Pre treatment | +++ | +++ |
| Post treatment (4 months) | +++ | − |
| Post treatment (5 months) | +++ | − |

Discussion

Biological assays which measure TGFα have shown that this growth factor is produced by a variety of transformed cell lines (1,2). TGFα has been isolated from conditioned media of melanoma cell lines, from urine of melanoma patients, and bovine pituitary cells. The use of biological assays cannot be used to measure TGFα since they do not distinguish TGFα from EGF. In addition, the apparent size heterogeneity of both EGF and TGFα resulting from processing of larger precursors further complicates the identification and characterization of these growth factors using biological assay (1, 2, 5, 12). To facilitate the identification of TGFα in biological samples we have developed a series of monoclonal antibodies which specifically react with TGFα and show no cross reactivity with EGF.

Monoclonal antibodies to TGFα were prepared in order to detect specific TGFα epitopes, determine the presence of TGFα in tumor cells and urine, and to develop an immunoassay which could distinguish TGFα from EGF. Purified, biologically active TGFα was found to be a poor immunogen reflecting its high amino acid conservation. Human TGFα differs from mouse TGFα by only 4 amino acid substitutions (5). For this reason several immunogens were used in order to generate adequate serum antibody titers for splenic fusions. The use of the recombinant trpE-TGFα 10 kd fusion protein generated the largest number of hybridomas indicating that the trpE sequence of the fusion protein is highly immunogenic in mice and probably acts as an adjuvant. Immunization with unfolded synthetic TGFα allowed the production of hybridomas useful for immunofluorescence and TGFα assay development. Immunizations with TGFα peptide (34-50) yielded hybridomas which are useful in certain assays such as immunoblotting.

The development of screening assays greatly facilitated the selection of hybridomas specific for TGFα. The assay using the polyclonal rabbit anti TGFα (34-50) to capture TGFα rapidly selects for antibodies which react with other epitopes on TGFα. The assay for the trpE-TGFα fusion protein can be considered a generic assay for screening hybridomas made against any fusion protein. It may also have utility as a test for screening antibodies against proteins or infectious agents in human blood such as AIDS, etc. In this assay format, human sera is incubated with anti-human IgG coated surface and washed. A trpE fusion protein engineered to contain the dominant epitope of the antigen is then incubated with the IgG coated surface and washed. The bound antigen is detected using a reporter antibody specific for the fusion protein. A positive signal will be obtained only if the human serum contains antibodies to the antigen of interest.

Many of the monoclonal antibodies produced are useful for immunoblotting TGFα. Monoclonal antibody 134A-2B3, generated from mice immunized with synthetic TGFα, is the most useful antibody for immunoblotting. Using conditioned media from melanoma cells and transformed rat fibroblasts we demonstrated that 134A-2B3 immunoblots 6 kd TGFα in melanoma cells and both a 6 kd and 18 kd TGFα in media from transformed rat fibroblasts. An 18 kd TGFα species has been previously shown to be produced by FeSV cells (23). The antibody also immunoblots TGFα which has been partially purified from the urine of a melanoma patient prior to treatment. After treatment, no TGFα was detected in the urine of the patient.

Monoclonal antibody 213-4.4 detects TGFα in tumor cells by indirect immunofluorescence. Analysis of A375 melanoma cells and FeSV transformed fibroblasts showed intense cytoplasmic staining of these cells. In contrast, no staining was detected using untransformed NIH-3T3 mouse fibroblasts. In addition antibody 213-4.4, is useful for histological staining of TGFα in paraffin-embedded sections of normal, and tumor tissue sections.

Monoclonal Antibody 137-178 and 134A-2B3 have been used to develop a two-site immunoradiometric assay specific for TGFα which has a sensitivity of 2 ng/ml. The assay can quantitate TGFα in fluids in the presence of high concentrations of EGF and was used to detect TGFα in conditioned media of A375 cells. The immunometric assay has clinial utility for measuring TGFα levels in the serum or urine of cancer patients in order to diagnose or monitor malignancy.

REFERENCES

1. Todaro, G. J., Delarco, J. E., and Cohen, S. (1976), Transformation by murine and feline sarcoma viruses specifically blocks binding of epidermal growth factor to cells, Nature, 264:26.
2. Sporn, M. B. and Todaro, G. J., (1980) Autocrine secretion and malignant transformation of cells. New Engl. J. of Med., 303:878.
3. De Larco, J. E. and Todaro, G. J., (1978) Growth factors from murine sarcoma virus-transformed cells, Proc. Natl. Acad. Sci. USA, 75:4001.
4. Anzano, M. A., Robert, A. B., Smith, J. M., Sporn, M. B. and De Larco, J. E., (1983) Sarcoma growth factor from conditioned medium is composed of both type alpha and type beta transforming growth factors, Proc. Natl. Acad. Sci. USA, 80:6264.
5. Marquardt, H. and Todaro, G. J., (1982) Human transforming growth factor Production by a melanoma cell line, purification and initial characterization J. Biol. Chem., 257:5220.
6. Marquardt, H., Hunkapiller, M. W., Hood, L. and Todaro, G. J., (1984) Rat transforming growth factor type 1: Structure and relation to epidermal growth factor Science, 223:1079.
7. Derynck, R., Roberts, A. B., Winkler, M. E., Chen, E. Y. and Goeddel, D. V., (1984) Human transforming growth factor-alpha: precursor structure and expression in E. coli., Cell, 38:287.
8. Bringman, T. S., Lindquist, P. B. and Derynck, R., (1987) Different transforming growth factor-α species are derived from a glycosylated and palimtoylated transmembrane precursor, Cell, 48:429.
9. Derynck, R., Goeddel, D. V., Ullrich, A., Gutterman, J. V., Williams, R. D., Bringman, T. S. and Berger, W. H., (1987) Synthesis of messenger RNA for transforming growth factors α and β and the epidermal growth factor receptor by human tumors, Cancer Research, 47:793.
10. Yeh, Y-C., Tsai, J. F., Chuang, L. Y., Yeh, H. W. Tsai, J. H., Florine, D. L, and Taim, J. P., (1987) Elevation of transforming growth factor-α and its relationship to epidermal growth factor and α-fetal protein levels in patients with hepatocellular carcinoma, Cancer Res., 47:896.
11. Ellis, D. L., Dafka, S. P., Chow, J. C., Naney, L. B., Inman, W. H., McCadden, M. E. and King, L. E. Jr., (1987) Melanoma growth factors, acanthosis nigricans, the sign of Leser-Trelat and multiple acrochordons: A possible role for alphatransforming growth factor in cutaneous paraneoplastic syndromes, N. Engl. J. Med., 25:1582.
12. Sherwin, S. A., Twardzik, D. R., Bohn, W. H., Cockley, K. D. and Todaro, G. J., (1983) High-molecular weight transforming growth factor activity in the urine of patients with disseminated cancer, Cancer Res., 43:403
13. Kimball, E. S., Bohn, W. H., Cockley, K. D., Warren, T. C. and Sherwin, S. A., (1984) Distinct high-performance liquid chromatography patterns of transforming growth factor activity in urine of cancer patients as compared with that of normal individuals, Cancer Res. 44:3616-3619.
14. Lee, D. C., Rochford, R., Todaro, G. J. and Villareal, L., (1985) Developmental expression of rat transforming growth factor-α mRNA, *Molec. Cell Biol.*, 5:3644.

15. Coffey, R. J. Jr., Derynck, R., Wilcox, J. N., Bringman, T. S., Goustin, A. S., Moses, H. L. and Pillelkow, M., (1987) Production and auto-induction of transforming growth factor-α in human keratinocytes, *Nature*, 238:817.

16. Kobrin, M. S., Asa, S. L., Samsoondar, J., Kudlow, J. E., (1987) α-Transforming growth factor in the bovine anterior pituitary gland: Secretion by dispersed cells and immunohistochemical localization, *Endocrinology*, 121:1412.

17. Kudlow, J. E., Korbrin, M. E., Purchio, A. F., Twardzik., D. R., Hernandez, E. R., Asa, S. L. and Adashi, E. Y., (1987) Ovarian transforming growth factor-α gene expression: immunohistochemical localization to the theca-interstitial cells, *Endocrinology*, 121:1577.

18. Kobrin, M. S., Samsoondar J., Kudlow, J. E., (1986) α-Transforming growth factor secreted by untransformed bovine anterior pituitary cells in culture. II. Identification using a sequence-specific monoclonal antibody, *J. Biol. Chem.*, 261:14414.

19. Gottlieb, A. B., Chang, C. K., Posnett, D. N., Fanelli, B., and Tam, J. P., (1988) Detection of transforming growth factor α in normal, malignant, and hyperproliferature human keratinocytes, *J. Exp. Med.*, 167:670.

20. Tam, J. P., SHeika, M. A., Solomon, D. S., Ossowski, L., (1986) Efficient synthesis of human type a-transforming growth factor: its physical and biological characterization, *Proc. Natl. Acad. Sci. USA.*, 83:8082.

21. Linsley, P. S., Hargreaves, W. R., Twardzik, D. R. and Todaro, G. J., (1985) Detection of larger polypeptides structurally and functionally related to type I transforming growth factor, *Proc. Natl. Acad. Sciences USA*, 82:356.

22. Winkler, M. E., Bringman, T., Marks, B. J., (1986) The purification of fully active recombinant transforming growth factor-α produced in *Escherichia coli*, *J. Biol. Chem..*, 261:13838.

23. Laemmli, U. K., (1970) Cleavage of structural proteins during assembly of the head of bacteriophage T4, *Nature*, 277:680–685.

24. Towbin, H., Staehelin, T. and Gordon, G., (1979) Electrophoretic transfer of proteins from polyacrylamide gels to nitrocellulose sheets: Procedure and some applications, *Proc. Natl. Acad. Sci. U.S.A.*, 76:4350–4354.

25. Ignotz, R. A., Kelly B., Davis, R. J., and Massague, J., (1986) Biologically active precursor for transforming growth factor type a released by retrovirally transformed cells, *Proc. Natl. Acad. Sci. USA*, 83:6307.

What is claimed is:

1. A method of detecting TGFα in formalin-fixed, paraffin-embedded human tissue sections which comprises:
   (1) contacting the tissue sections with a monoclonal antibody, which
      (a) specifically forms a complex with TGFα in formalin-fixed, paraffin-embedded tissue sections,
      (b) has an affinity of at least $10^7$, and
      (c) is directed to the epitope to which monoclonal antibody 213-4.4 (ATCC No. HB9992) is directed,
   under conditions such that the antibody binds to the tissue sections, and
   (2) detecting the bound antibody and thereby detecting TGFα in the tissue sections.

2. A method of claim 1, wherein the monoclonal antibody is labeled with a detectable marker.

3. A method of claim 1, wherein the monoclonal antibody bound to the tissue sections is detected by:
   (1) contacting the monoclonal antibody with a detectably labeled second antibody under conditions such that the second antibody binds to the monoclonal antibody, and
   (2) detecting the second antibody so bound.

4. A method of claim 1, wherein the tissue sections are of a tissue in which normal tissue is characterized by the absence of TGFα and neoplastic tissue is characterized by the presence of TGFα in a subset of such neoplastic tissue.

5. A method of claim 4, wherein the tissue is breast tissue and the neoplastic tissue is a breast carcinoma.

6. A method of claim 4, wherein the tissue is skeletal muscle tissue and the neoplastic tissue is a myogenic tumor.

7. A method of detecting TGFα in formalin-fixed, paraffin-embedded sections of a human tissue in which normal human tissue is characterized by a difference in the amount of TGFα relative to the amount present in neoplastic tissue, which comprises:
   (1) contacting the tissue sections with monoclonal antibody 213-4.4 (ATCC No. HB9992) under conditions such that the antibody binds to the tissue sections,
   (2) detecting the antibody bound to the tissue sections, and
   (3) thereby detecting TGFα in the tissue sections.

8. A method of diagnosing a neoplastic or preneoplastic condition in a human subject which comprises:
   (1) obtaining from the subject a sample of a tissue,
   (2) preparing tissue sections from the tissue,
   (3) detecting TGFα in such tissue sections using the method of claim 7, and
   (4) thereby diagnosing such neoplastic or preneoplastic condition.

9. A method of claim 7 or 8, wherein the tissue section is breast tissue.

10. A method of claim 7 or 8, wherein the tissue section is muscle tissue.

11. A method of determining a difference in the amount of distribution of TGFα in a formalin-fixed, paraffin-embedded human tissue section from a tissue to be tested relative to the amount and distribution of TGFα in a tissue section from a normal tissue which comprises:
   (1) contacting the tissue section to be tested and the normal tissue section with a monoclonal antibody, which
      (a) specifically forms a complex with TGFα in formalin-fixed, paraffin-embedded tissue sections,
      (b) has an affinity of at least $10^7$, and
      (c) is directed to the epitope to which monoclonal antibody 213-4.4 (ATCC No.. HB9992) in directed,
   under conditions such that the antibody binds to the tissue sections,
   (2) determining the amount and distribution of antibody bound to the tissue sections, and (3) thereby determining the difference in the amount and distribution of TGFα in the tissue sections.

12. A method of diagnosing a neoplastic or preneoplastic condition in a human subject which comprises:
   (1) obtaining from the subject a sample of a tissue,
   (2) preparing tissue sections from the tissue,
   (3) detecting TGFα in such tissue sections using the method of claim 11, and
   (4) thereby diagnosing such neoplastic or preneoplastic condition.

13. A method of claim 12, wherein the tissue is breast tissue.

14. A method of claim 12, wherein the tissue is muscle tissue.

* * * * *